US00PP37267P3

(12) United States Plant Patent
Mehlenbacher

(10) Patent No.: US PP37,267 P3
(45) Date of Patent: Feb. 17, 2026

(54) ***CORYLUS* PLANT NAMED 'Thompson'**

(50) Latin Name: *Corylus avellana*
Varietal Denomination: 'Thompson'

(71) Applicant: Oregon State University, Corvallis, OR (US)

(72) Inventor: Shawn A. Mehlenbacher, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 177 days.

(21) Appl. No.: 18/484,961

(22) Filed: Oct. 11, 2023

(65) Prior Publication Data

US 2025/0120360 A1 Apr. 17, 2025

(51) Int. Cl.

| | |
|---|---|
| ***A01H 5/08*** | (2018.01) |
| ***A01H 5/02*** | (2018.01) |
| ***A01H 6/00*** | (2018.01) |

(52) U.S. Cl.
USPC ..... Plt./152
CPC ..... *A01H 6/00* (2018.05); *A01H 5/02* (2013.01)

(58) Field of Classification Search
USPC ..... Plt./152
CPC ... A01H 5/10; A01H 5/08; A01H 5/00; A01H 6/00
See application file for complete search history.

(56) References Cited

PUBLICATIONS

UPOV Guidelines for the Conduct of Tests for Distinctness, Homogeneity and Stability Hazelnut TG/71/3, Mar. 28, 1979, 24 pp. (Year: 1979).*

* cited by examiner

*Primary Examiner* — June Hwu
(74) *Attorney, Agent, or Firm* — Klarquist Sparkman, LLP

(57) ABSTRACT

A new and distinct *Corylus avellana* plant is disclosed, distinguished by its low vigor, globose growth habit, production of nuts with round kernels that fall free of the husk at maturity, resistance to eastern filbert blight and big bud mite, S-alleles, nut size, kernel percentage, frequency of nut defects, time of pollen shed, and length of the husk or involucre.

7 Drawing Sheets

Specification includes a Sequence Listing.

ACKNOWLEDGMENT OF GOVERNMENT SUPPORT

This invention was made with government support under Specialty Crops Research Initiative Grant 2016-51181-25412 awarded by the USDA-National Institute of Food and Agriculture and under agreement 58-5358-4-025 awarded by USDA-Agricultural Research Service. The government has certain rights in the invention.

Latin name of the genus and species of the plant claimed: *Corylus avellana.*

Variety denomination: 'Thompson'.

INCORPORATION OF ELECTRONIC SEQUENCE LISTING

The Sequence Listing is submitted as an XML file named "Sequence.xml," created on Oct. 3, 2023, 35,809 bytes, which is incorporated by reference herein.

BACKGROUND

The present invention relates to a new and distinct cultivar of European hazelnut, also known as filbert, and botanically known as *Corylus avellana*, hereinafter referred to by the name 'Thompson'. The new *Corylus* plant resulted from a controlled cross of the female parent *Corylus avellana* 'OSU 914.082' (unpatented) x male parent *Corylus avellana* 'OSU 820.007' (unpatented) made in February 2005 (see, FIG. 1). A tree of 'OSU 914.082' was emasculated and covered to prevent foreign pollen contamination. Controlled pollinations used pollen of 'OSU 820.007'. Hybrid seeds resulting from the cross were harvested in August 2005. They were provided a period of moist chilling, subsequently germinated, and the seedlings were grown in the greenhouse during the summer of 2006. From this cross, a total of 93 seedling trees were planted in a research field in Corvallis, OR, in October 2006. 'Thompson' was discovered and selected as a single plant within that progeny of the stated cross-pollination. It was originally assigned the designation 'OSU 1304.039', which indicates the row and tree location of the original seedling.

The female parent is 'OSU 914.082', obtained from a cross of 'OSU 315.096' (unpatented) and 'Santiam' (unpatented, Mehlenbacher et al., *HortScience* 42:715-717, 2007). 'OSU 315.096' is from a cross of 'OSU 23.017' (unpatented) and 'Tonda Gentile delle Langhe' (unpatented) from northern Italy. 'OSU 23.017' is from a cross of 'Barcelona' (unpatented) and 'Extra Ghiaghli' (unpatented). 'Barcelona' is an old *Corylus avellana* cultivar from Spain that is widely distributed in Europe and was introduced to the U.S. in about 1885 (Mehlenbacher and Miller, *Fruit Var. J.* 43:90-95, 1989). 'Barcelona' is known under several different names, including 'Castanyera' in Tarragona (Spain), 'Grande' in Asturias (Spain), 'Grada de Viseu' in Portugal, and 'Fertile de Coutard' in France. 'Extra Ghiaghli', described by Raptopolous and Kantartzis (1961), is a clone of the important Turkish cultivar 'Tombul' and was imported from Greece in the late 1950s. 'Santiam' is a parent of 'McDonald' (U.S. Plant Pat. No. 28,200).

The male parent is 'OSU 820.007', an unreleased selection from a cross of 'OSU 275.031' x 'OSU 504.065' (both unpatented). 'OSU 275.031' is from a cross of 'Montebello' (unpatented) from Sicily and 'OSU 74.037' (unpatented). The parentage of 'OSU 74.037' includes 'Barcelona', 'Daviana' (unpatented) from England and 'Tombul Ghiaghli' (unpatented), a Turkish type from Greece (Raptopolous and Kantartzis, 1961). 'OSU 504.065' is a parent of 'York' (U.S. Plant Pat. No. 24,972). The pedigree of 'OSU 504.065' includes 'Montebello', grower selection 'Compton' (unpatented), an unknown selection labeled F-4, and 'Gasaway' (unpatented, Mehlenbacher et al., *HortScience* 26:410-411, 1991), the original donor of resistance to eastern filbert blight.

'Thompson' was asexually reproduced by rooted suckers in 2012 through 2021 in Corvallis, OR. The unique features of this new *Corylus* are stable and reproduced true-to-type in successive generations of asexual reproduction.

SUMMARY

The following traits have been observed and are determined to be the unique characteristics of 'Thompson'. These characteristics in combination distinguish 'Thompson' from other know *Corylus avellana* cultivars, such as 'Yamhill' (unpatented, Mehlenbacher et al., *HortScience* 44:845-847, 2009), 'Jefferson' (unpatented, Mehlenbacher et al., *HortScience* 46:662-664, 2011), 'McDonald' (U.S. Plant Pat. No. 28,200), 'Wepster' (U.S. Plant Pat. No. 27,141), 'Barcelona', and 'Tonda di Giffoni' (unpatented), and other cultivars and selections of *Corylus avellana* known to the inventor:

1. Low vigor and globose plant habit.
2. High level of resistance to eastern filbert blight (EFB) caused by the fungus *Anisogramma anomala* (Peck) E. Müller. The source of this resistance is a single dominant allele conferred from 'Gasaway', which protects *Corylus avellana* 'McDonald', 'Wepster', 'Dorris' (U.S. Plant Pat. No. 25,022), 'Jefferson', 'Yamhill', and several other *Corylus avellana* cultivars and pollinizers.
3. Expression of incompatibility alleles $S_2$ and $S_{15}$ in the styles and $S_{15}$ in the pollen.
4. High resistance to big bud mites (primarily *Phytoptus avellanae* Nal.).
5. Other distinguishing characteristics include nut size, kernel percentage (ratio of kernel weight to nut weight), frequency of defects (blank nuts, moldy kernels, twin kernels, etc.), time of pollen shed, and length of the husk or involucre.

Female Receptivity: The female inflorescences of 'Thompson' emerge early and are fully receptive in mid-January, with 'McDonald', but their styles blacken about two weeks earlier than those of 'McDonald' (see, FIGS. 5-7).

Pollen Shed: 'Thompson' generally sheds pollen in Corvallis, OR in early mid-season, with 'McDonald' and before 'Felix' (U.S. Plant Pat. No. 24,973) (see, FIGS. 5-7).

Husk Length: The husk of 'Thompson' is about 1.3 times nut length, slightly shorter than 'Barcelona', while 'Wepster' is 2.0 times nut length. The husks have finger-like tips, are slit down the side, and flare open as they dry at maturity (see, FIG. 3). About 92% of the nuts fall free of the husk at maturity.

Nuts and Kernels: 'Thompson' produces round, medium-sized nuts and kernels. Most of the pellicle is removed from the kernel with dry heat in the blanching process (see, FIG. 4). The combination of correct size, round shape and good blanching make 'Thompson' well-suited to the kernel market for use in confections and baked goods.

The foregoing and other objects and features of the disclosure will become more apparent from the following detailed description, which proceeds with reference to the accompanying figures.

BRIEF DESCRIPTION OF THE DRAWINGS

The accompanying color photographs illustrate the overall appearance of the new variety, showing the colors as true as it is reasonably possible to obtain in colored reproductions of this type. It should be noted that colors may vary, for example due to lighting conditions at the time the photograph is taken. Therefore, color characteristics of this new variety should be determined with reference to the observations described herein, rather than from the photographs alone.

FIG. 5 shows the time of female receptivity (bottom, red), pollen shed (top, green), and vegetative budbreak of 'Thompson' (OSU 1304.039), 'McDonald' and other hazelnut cultivars in Corvallis, OR (December 2018 to March 2019).

FIG. 6 shows the time of female receptivity (bottom, red), pollen shed (top, green), and vegetative budbreak of 'Thompson' (OSU 1304.039), 'McDonald' and other hazelnut cultivars in Corvallis, OR (December 2019 to March 2020).

FIG. 7 shows the time of female receptivity (bottom, red), pollen shed (top, green), and vegetative budbreak of 'Thompson' (OSU 1304.039), 'McDonald' and other hazelnut cultivars in Corvallis, OR (December 2020 to March 2021).

SEQUENCE LISTING

Figure 1:
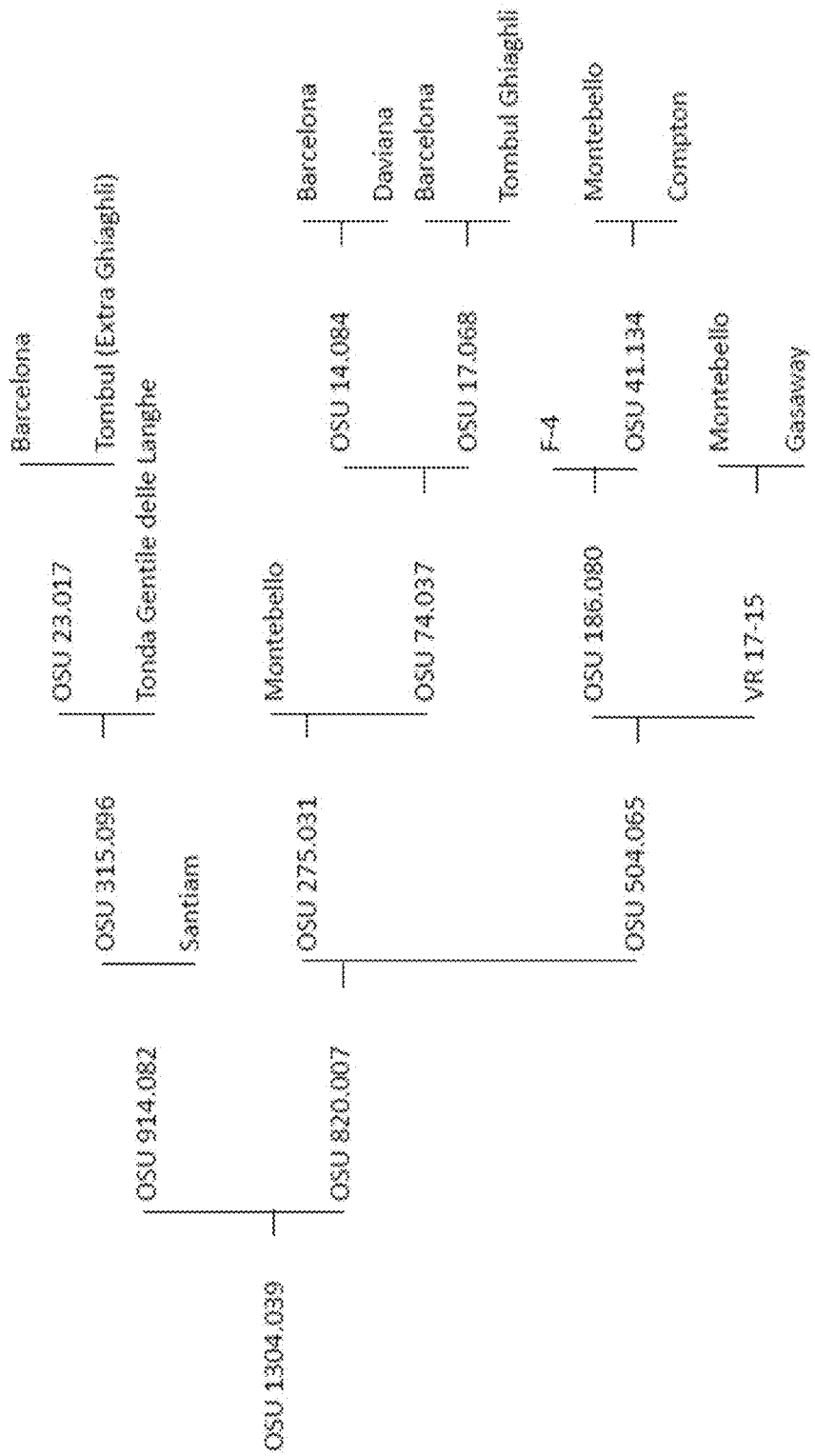
FIG. 1 shows the pedigree of new cultivar 'Thompson' (OSU 1304.039).
Figure 2:
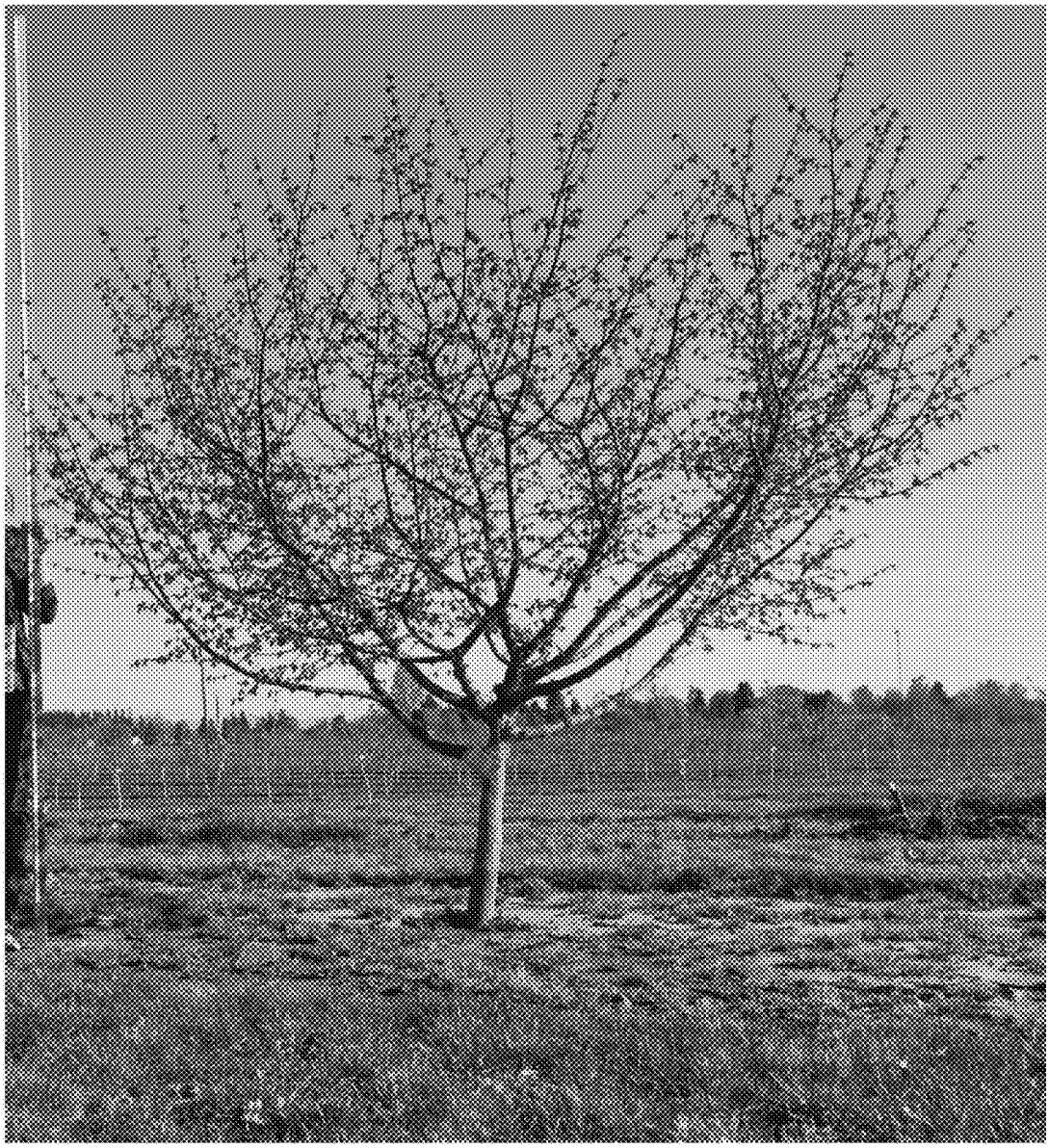
FIG. 2 shows a 7-year-old tree of the new hazelnut cultivar 'Thompson'. The photo was taken on Jun. 17, 2022, in the eighth leaf pruned to a single trunk.

The nucleic acid sequences in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing SEQ ID NOS: 1-40 are primer sequences that can be used for genetic fingerprinting (see, Table 7).

DETAILED DESCRIPTION

Certain characteristics of this variety may change with changing environmental conditions (such as photoperiod, temperature, moisture, soil conditions, nutrient availability, or other factors) without, however, any variance in genotype. Color descriptions and other terminology are used in accordance with their ordinary dictionary descriptions unless the context clearly indicates otherwise. The aforementioned photographs and following observations and measurements describe plants grown in Corvallis, OR, outdoors in the field during the spring and summer. The plant used for the photographs and description were from a seven-year-old tree propagated by tie-off layerage and growing on its own roots. In the following description, color references are made to The Royal Horticultural Society Colour Chart, 5$^{th}$ Edition, 2007 except where general terms of ordinary dictionary significance are used. The color values were determined in spring and summer 2020-2022 under natural light conditions in Corvallis, Oregon. The UPOV descriptor list is from the Mar. 28, 1979 Hazelnut guidelines from UPOV.

BOTANICAL

Scientific name: *Corylus avellana.*

Parentage:

- *Seed parent.*—'OSU 914.082' (unpatented breeding selection).
- *Pollen parent.*—'OSU 820.007' (unpatented breeding selection).

Incompatibility alleles: 'Thompson' has incompatibility alleles $S_2$ and $S_{15}$. Hazelnut is a wind-pollinated, monoecious species that exhibits a sporophytic self-incompatibility system controlled by a single locus designated as the S-locus with 33 alleles (Mehlenbacher, *J. Amer. Soc. Hort. Sci.* 139:191-212, 2014). For comparison, *Corylus avellana* 'McDonald' has the same pair of alleles $S_2$ and $S_{15}$, 'PollyO' (U.S. Plant Pat. No. 32,459) has alleles $S_2$ and $S_{10}$, 'Sacajawea' (unpatented, Mehlenbacher et al., *HortScience* 43:255 257, 2008) has the alleles $S_1$ and $S_{22}$, 'Tonda di Giffoni' has alleles $S_2$ and $S_{23}$, while 'Tonda Pacifica' (U.S. Plant Pat. No. 22,715) and 'Wepster' have alleles $S_1$ and $S_2$.

Propagation (type rooted suckers):

- *Time to initiate roots.*—About 30 days at 20° C.
- *Time to produce a rooted young plant.*—About six months at 22° C.
- *Root description.*—Fine to thick; freely branching; creamy white in color.

Propagation (type whip grafting):

- *Time to budbreak on the scions.*—About 14 days at 25° C.
- *Time to produce a grafted plant.*—About six months at 25° C.

Plant:

- *Appearance.*—Natural habit is perennial shrub, but in commercial orchards, is a single trunk tree. Globose plant habit.
- *Growth and branching habit.*—Freely branching; about 15 lateral branches develop per plant. Pinching, that is, removal of the terminal apices, enhances branching with lateral branches potentially forming at every node.
- *Vigor.*—Low.
- *Plant height.*—About 2.9 m.
- *Plant diameter.*—About 3.1 m.
- *Trunk cross section area 30 cm above the soil line.*—In a trial planted in Corvallis, Oregon in 2014, trunk cross-sectional area was 46.9 cm$^2$ in December 2020. In a second trial planted in Corvallis, OR in 2015, trunk cross-sectional area was 47.0 cm$^2$. These values are about 65% of 'Jefferson' in the same trials.
- *Trunk color.*—RHS 197B.

Lateral branch:

- *Length.*—19.0-31.0 cm, typically 27.2 cm.
- *Diameter.*—3.3-4.5 mm, typically 3.7 mm.
- *Internode length (at base).*—About 0.75 cm.
- *Internode length (at tip).*—2.4-3.5 cm, typically about 2.8 cm.
- *Texture.*—Smooth, pubescent.
- *Strength.*—Strong.
- *Color.*—Immature: RHS 144A. Mature: RHS 177B. Previous Seasons Branches: RHS 199C.

Foliage:

- *Arrangement.*—Alternate, simple.
- *Size.*—Length: 7.5-11.9 cm, typically about 9.7 cm. Width: 7.4-11.1 cm, typically about 8.8 cm.
- *Shape.*—Oblong to ovate.
- *Apex.*—Obtuse to acute.
- *Base.*—Cordate.
- *Margin.*—Serrate.
- *Leaf texture.*—Slightly pubescent on upper and lower surfaces.
- *Foliage color.*—Developing Foliage: Upper Surface: RHS 141B. Lower Surface: RHS 141C. Fully Expanded Foliage: Upper Surface: spring and summer, RHS 137B; late summer and fall, RHS 137B. Lower Surface: spring and summer, RHS 137D; late summer and fall, RHS 137D.
- *Venation pattern.*—Pinnate.
- *Venation color.*—Upper Surface: Spring and summer, RHS 145A; late summer and fall, RHS 145A. Lower Surface: Spring and summer, RHS 145A; late summer and fall, RHS 145A.
- *Leaf bud.*—Shape: Globular, UPOV Descriptor value-2. Time of Budbreak: Medium, UPOV Descriptor value — 5. 'Thompson'. budbreak is about 12 days before 'Jefferson', 6 days before 'Felix', and 6 days later than 'McDonald'. Color of leaf buds: RHS 144C.
- *Petiole.*—Length: 13.0-19.3 mm, typically about 16.3 mm. Diameter: 0.8-1.8 mm, typically about 1.3 mm. Texture: Weakly pubescent (both upper and lower surfaces). Color: RHS 143B (lower surface, early fall).

Flowers:

- *Male inflorescences.*—Catkins Color Prior to Elongation: RHS 176B exposed to sun, RHS 194C in shade. Catkin Length: 23.5 mm.
- *Female inflorescence style color.*—RHS 59A.
- *Female inflorescence stigma color.*—RHS 59A.
- *Time of female flowering.*—Early-medium, UPOV Descriptor value — 4.
- *Time of female flowering compared to male flowering.*—Homogamy, UPOV Descriptor value — 2.

*Involucre constriction*.—Present.

*Involucre length*.—1.3 times length of nut, UPOV Descriptor value — 5.

*Involucre size of indentation*.—Strong, UPOV Descriptor value — 7.

*Strength of involucre serration of indentation*.—Weak, UPOV Descriptor value — 3.

*Thickness of involucre callus at base*.—Thin, UPOV Descriptor value — 3.

*Pubescence on husk*.—Absent, UPOV Descriptor value — 1.

*Density of hairiness of involucre*.—Weak, UPOV Descriptor value — 3.

*Jointing of involucre bracts*.—Absent, UPOV Descriptor value — 1.

*Involucre color*.—RHS 145A for inner and outer surface.

Nut:

*Length*.—Average 17.1 mm.

*Width*.—Average 18.6 mm.

*Depth*.—Average 16.8 mm.

*Nut shape*.—Globular, UPOV Descriptor value — 1.

*Nut shape index*.—1.04 ((Width+Depth)/2*Length).

*Nut compression index*.—1.10 (Width/Depth).

*Nut weight*.—2.79 g.

*Kernel weight*.—1.25 g.

*Kernel percentage*.—44.8% (Kernel Weight/Nut Weight).

Figure 3:
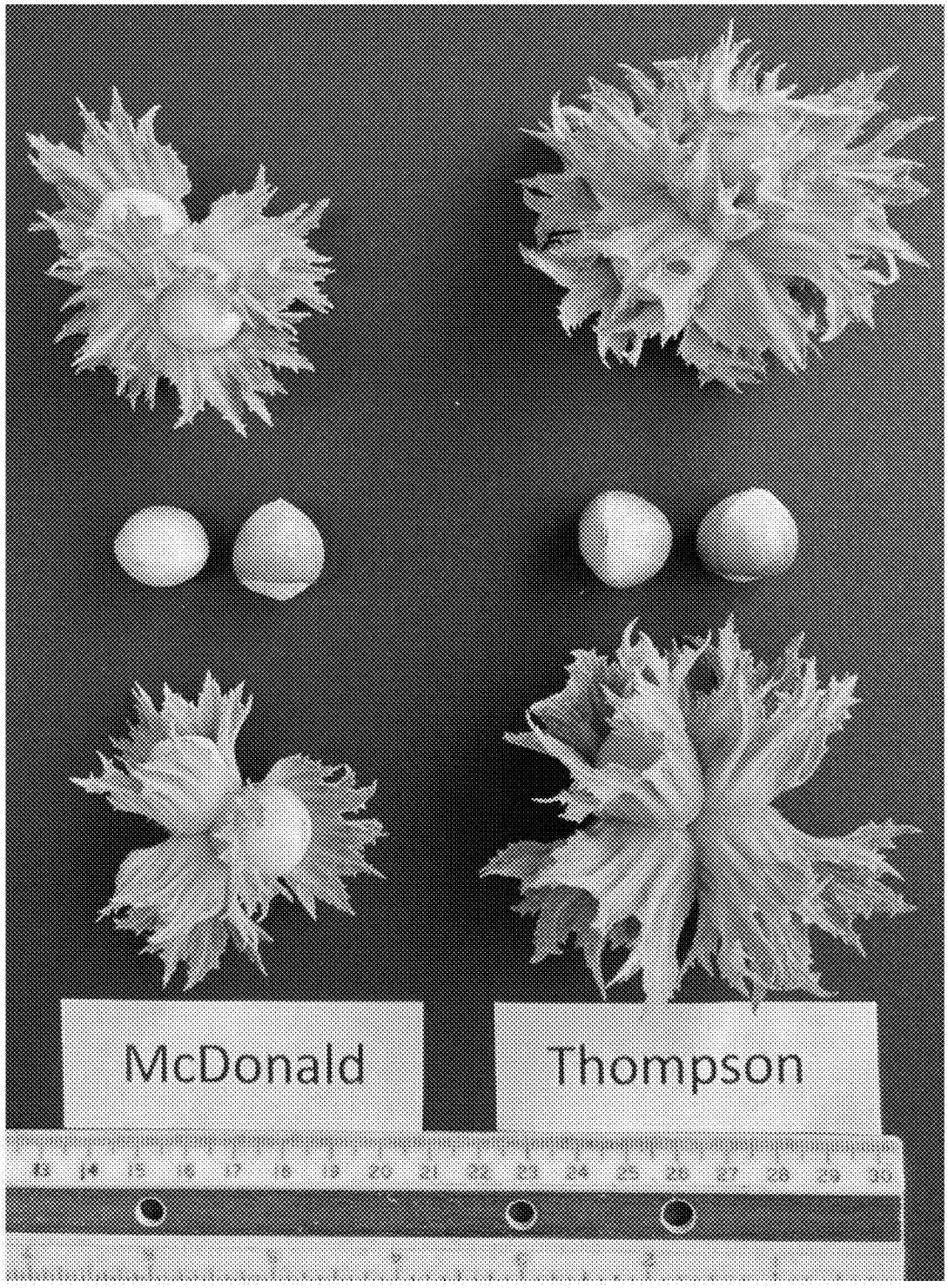
FIG. 3 shows immature nuts and husks of 'Thompson' and 'McDonald' hazelnuts.

*Number of fruits per cluster*.—Three to four (see, FIG. 3).

*Nutshell coloration*.—RHS 164A.

*Number of stripes on shell*.—Many, UPOV Descriptor value — 7.

*Shape of fruit apex*.—Slightly prominent, UPOV Descriptor value — 3.

*Prominence of fruit apex*.—Slightly prominent, UPOV Descriptor value — 3.

*Size of fruit pistil scar on shell*.—Small, UPOV Descriptor value — 3.

*Hairiness of top of fruit*.—Weak, UPOV Descriptor value — 3.

*Curvature of nut basal scar*.—Flat, UPOV Descriptor value — 2.

*Double kernels*.—Absent.

*Kernel apex shape*.—Obtuse, UPOV Descriptor value — 2.

*Kernel base shape*.—Rounded, UPOV Descriptor value — 2.

*Kernel shape*.—Globular, UPOV Descriptor value — 1.

*Shape of kernel in cross-section*.—Circular, UPOV Descriptor value — 2.

*Lateral groove in kernel*.—Absent, UPOV Descriptor value — 1.

*Corkiness of pellicle of kernel*.—Slightly corky, UPOV Descriptor value — 3.

*Color of pellicle*.—RHS 165C.

*Color of kernal after roasting* (130° *C. for* 15 *minutes*).—RHS 158A.

Disease/pest resistance: In Oregon, plants of 'Thompson' are resistant to EFB caused by the fungus *Anisogramma anomala* (Peck) E. Müller. All trees of 'Thompson' in trial plots have remained free of EFB with no fungicide applications. Fungicide applications are not expected to be needed to control EFB. Plants have not been challenged against all populations of *Anisogramma anomala* present in North America (Muehlbauer et al., *Phytopathology* 109:1074-1082, 2019); it is likely that 'Thompson' is susceptible to populations of the fungus in New Jersey that are able to overcome resistance derived from 'Gasaway'. Susceptibility to bacterial blight caused by *Xanthomonas arboricola* pv. *corylina* has not been quantified, but no trees in the trials in Corvallis, Oregon were affected. Susceptibility to bud mite (primarily *Phytoptus avellanae* Nal.) was rated in trials in Corvallis, OR, in mid-December on a scale of 1 (no blasted buds) to 5 (many blasted buds). The average rating for 'Thompson' was 1.04, indicating a high level of resistance comparable to 'Barcelona' and 'Jefferson'.

Temperature tolerance: 'Thompson' was selected in Corvallis, OR and is targeted for production in USDA Plant Hardiness Zones 6a to 7b. Plants of the new *Corylus avellana* have been observed to tolerate temperatures from −18° C. to 40° C.

Comparative data:

*Disease resistance*.—Based on field exposure and DNA markers, 'Thompson' is resistant to eastern filbert blight (EFB) caused by *Anisogramma anomala* in Oregon, where cultivars previously widely grown ('Barcelona', 'Ennis' (unpatented), 'Daviana', and 'Butler' (unpatented)) are susceptible. The more recently developed cultivars 'Santiam', 'Yamhill', 'Jefferson', 'Dorris', 'Wepster', and 'McDonald' and their associated pollinizers are protected from EFB by a single resistance gene from *Corylus avellana* 'Gasaway'. This gene provides a high level of resistance in Oregon and Washington where the diversity of the fungus is limited (Muehlbauer et al., *Phytopathology* 109:1074-1082, 2019), but does not provide a similar level of protection from disease in the eastern U.S. where the pathogen is endemic and genetically diverse (Capik and Molnar, *J. Amer. Soc. Hort. Sci.* 137:157-172, 2012; Molnar et al., *Plant Dis.* 10:1265, 2010; Muehlbauer et al., *Phytopathology* 109:1074-1082, 2019). It is unlikely that 'Thompson' would remain free of EFB in New Jersey where populations of the pathogen are genetically diverse.

Figure 4:
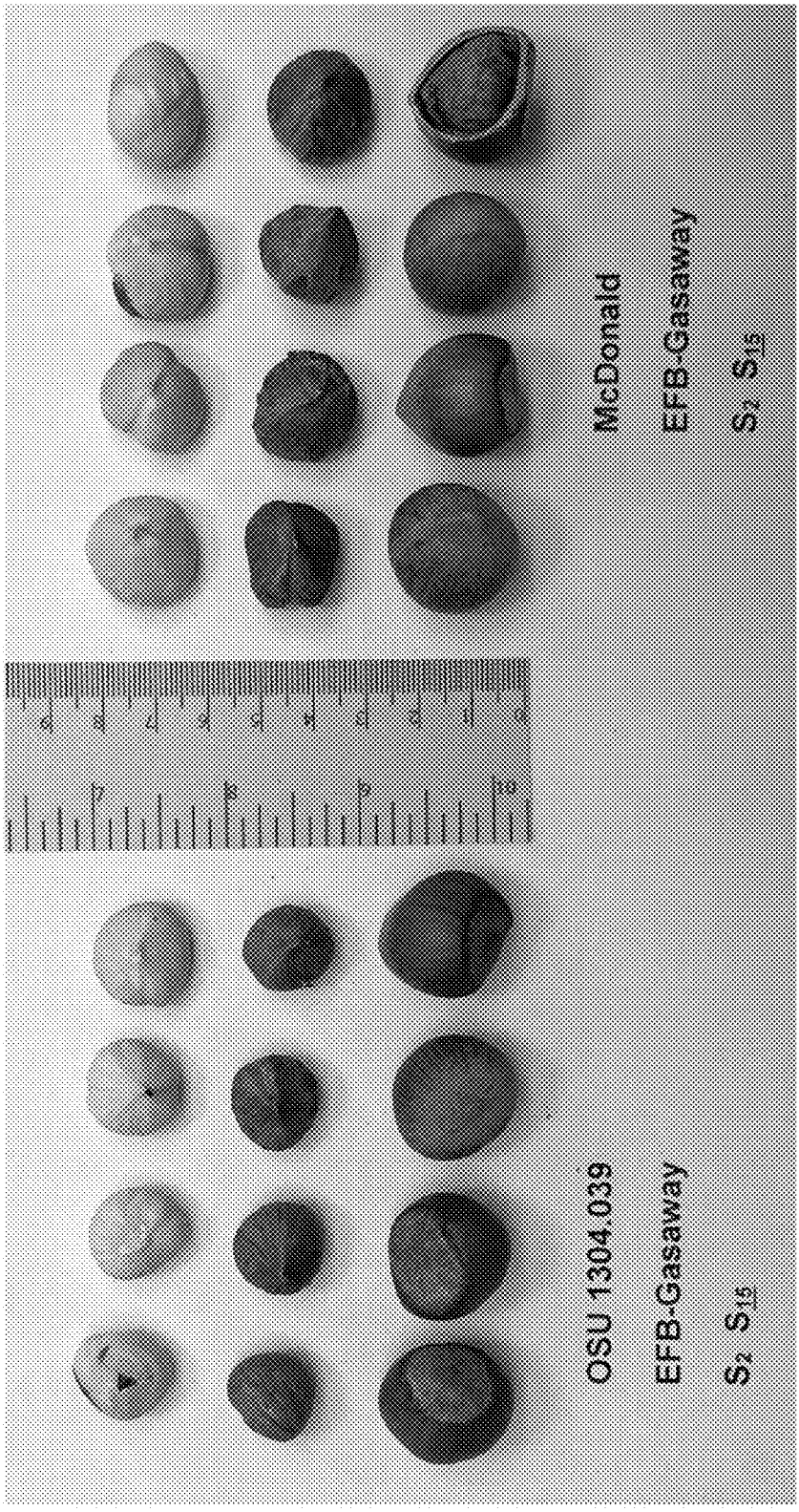
FIG. 4 shows nuts, raw kernels, and blanched kernels of hazelnuts of 'Thompson' (OSU 1304.039) and 'McDonald' hazelnuts. "EFB-Gasaway" indicates that both 'Thompson' and 'McDonald' carry a dominant allele for eastern filbert blight resistance from 'Gasaway', and "$S_2$ $S_{15}$" indicates that 'Thompson' and 'McDonald' carry incompatibility alleles 2 and 15.

*Nut and kernel characteristics*.—'Thompson' hazelnut is targeted for the blanched kernel market and specifically for nut production in the Pacific Northwestern United States in USDA Plant Hardiness Zones 6a to 7b. As shown in FIGS. 3 and 4, the nut shape and kernel shape are round. The average single nut weight for 'Thompson' over four years (2017-20) is 2.79 g, average single kernel weight is 1.25 g, with an average kernel percentage of 44.8% (see, Table 3). Nut weight in the same trial was 3.86 g for 'Jefferson', 2.70 g for 'McDonald' and 2.43 g for 'Wepster'. Kernel weights in the same trial were 1.74 g for 'Jefferson', 1.41 g for 'McDonald' and 1.13 g for 'Wepster'. Kernel percentage in the same trial was 45.0% for 'Jefferson', 52.2% for 'McDonald' and 46.7% for 'Wepster'. 'Thompson' nuts and kernels are significantly smaller than those of 'Barcelona' and 'Jefferson', and intermediate between 'McDonald' and 'Wepster'. In the trial planted in 2014 in Corvallis, OR, the trees produced a few nuts in 2016, but were not harvested. Nuts were harvested for four years (2017-20), dried, weighed and evaluated. Total nut weight per tree (2017-20) was 14.7 kg for 'Thompson', compared to the checks 'Jefferson' (18.3 kg), 'McDonald' (18.6 kg) and 'Wepster' (21.8 kg). Trunk cross-sectional area (TCA) was 46.89 cm2, or 66% of 'Jefferson'. Yield efficiency, the ratio of total yield to TCA, was a very high 0.315 kg/cm$^2$ and higher than all three checks. Trees have a globose growth habit, and lower vigor than all other selections in the Corvallis trial. — Raw kernels of 'Thompson' have a light brown pellicle with little attached fiber (average rating was 2.19 on a scale of 1 (no fiber) to 4 (much fiber); see, Table 3). Pellicle removal after roasting at 150° C. for 15 min and rubbing is rated on a scale of 1 (complete pellicle removal) to 7 (no pellicle removal). Most of the pellicle on 'Thompson' kernels is removed after roasting with an average rating of 2.75 (see, Table 3), a value slightly better than 'McDonald' (3.50) and 'Wepster' (3.03). — The average percentage of good kernels (kernels free of defects) for 'Thompson' in the trial planted in 2014 was 83.2% (see, Table 3). There was on average 4.2% blank nuts, 2.8% moldy kernels, 1.6% nuts with shriveled kernels, and 7.4% poorly filled nuts. The percentage of good kernels for 'Thompson' was considerably higher than the 60-70% range in multiple reports for 'Barcelona' in Oregon. The percentage of poorly filled nuts for 'Thompson' (7.4%) was lower than for 'Jefferson' (12.6%) and 'Wepster' (17.3%) despite the heavy crop loads on 'Thompson' trees.

*Nut maturity date.*—The nuts of 'Thompson' are typically borne in clusters of 3-4 in husks about 30% longer than the nuts (see, FIG. 3). The husks open as they dry at maturity. About 92% of the nuts fall free of the husk at maturity and the other 8% of the nuts come out of the husks as they moved through the harvester. When mature, the shells are tan in color. Estimates recorded at the time of harvest in the two trials indicate that 'Thompson' nuts mature about 3 days before 'Barcelona', 6 days before 'Jefferson', 7 days after 'Wepster', and 10 days after 'McDonald'.

*Flowering time.*—Trees of 'Thompson' set a high number of catkins that shed copious amounts of pollen. Time of pollen shed and female receptivity were recorded weekly from mid-December to mid-March in the second trial for three years for 'Thompson' and the check cultivars (see, FIGS. 5-7). The female inflorescences of 'Thompson' emerge early and are fully receptive in mid-January, with 'McDonald', but their styles blacken about two weeks earlier than those of 'McDonald'. Female receptivity dates are similar for 'Wepster', 'Yamhill', 'York' and 'PollyO'. Pollen is shed by 'Thompson' in early mid-season, with 'McDonald' and before 'Felix'. Pollen has been collected and used in several controlled pollinations, and both quantity and viability appear to be very good. Pollen germination tests over three years (2018-2020) showed good germination for 'Thompson'. On Jan. 23, 2020, pollen germination of 'Thompson' was 79% in contrast to 40% for 'Barcelona' while values for other cultivars ranged from 69 to 91%. On Jan. 30, 2019, pollen germination of 'Thompson' was 76% and similar to 'PollyO' (72%), 'Sacajawea' (82%) and 'Yamhill' (72%). Pollen germination tests on five dates in January 2018 showed good germination for 'Thompson' (65%), 'PollyO' (77%), 'Sacajawea' (73%) and 'Yamhill' (81%), and much lower germination for 'Barcelona' (40%). When establishing a new orchard, the inclusion of at least three pollinizers with the main cultivar is encouraged.

*Additional comparative descriptors.*—Tables 1-6 provide additional descriptors and trial data distinguishing 'Thompson' from various hazelnut varieties.

*Microsatellite marker analysis.*—Twenty microsatellite (simple sequence repeat) markers were used. PCR products were multiplexed post-PCR and sized using capillary electrophoresis. See, for example, Bassil et al., *Acta Horticulturae* 686:105-110, 2005; Gökirmak et al., *Genetic Resources and Crop Evolution* 56:147-172, 2009; Gürcan and Mehlenbacher. *Molecular Breeding* 26:551-559, 2010; Gürcan et al. *Tree Genetics and Genomes* 6:513-531, 2010). The microsatellite markers are described in Table 7 and allele sizes are reported in Table 8.

TABLE 1

Nut yield, trunk cross-sectional area (TCA), yield efficiency, and bud mite ratings of 'Thompson' in comparison with other hazelnut cultivars and selections in the first trial, planted in 2014. Randomized complete block design with four blocks and a single tree of each selection in each block. Yield is in kg per tree. Trunk cross-sectional area (TCA) is in cm$^2$. Yield efficiency is in kg/cm$^2$. Bud mite ratings are from 1 (no blasted buds) to 5 (many blasted buds).

| | Nut Yield (kg) | | | | |
|---|---|---|---|---|---|
| Selection | 2017 | 2018 | 2019 | 2020 | Total |
| '541.147' | 0.367 | 2.875 | 4.758 | 3.670 | 11.669 |
| 'Thompson' | 1.784 | 2.945 | 3.623 | 6.353 | 14.704 |
| 'Jefferson' | 2.389 | 4.765 | 4.596 | 6.585 | 18.335 |
| 'McDonald' | 0.782 | 3.895 | 5.858 | 8.323 | 18.857 |
| 'Wepster' | 2.161 | 4.590 | 5.325 | 9.695 | 21.771 |
| LSD (0.05) | 0.581 | 0.948 | 1.114 | 1.395 | 2.551 |

| Selection | TCA | Yield efficiency | BBM |
|---|---|---|---|
| '541.147' | 71.13 | 0.1647 | 3.4 |
| 'Thompson' | 46.89 | 0.3151 | 1.0 |
| 'Jefferson' | 71.22 | 0.2581 | 1.2 |
| 'McDonald' | 79.59 | 0.2386 | 2.0 |
| 'Wepster' | 77.33 | 0.2867 | 1.5 |
| LSD (0.05) | 13.34 | 0.0448 | 0.2 |

TABLE 2

Nut weight, kernel weight, percent kernel, and ratings for fiber and blanching (pellicle removal) of 'Thompson' in comparison with other hazelnut cultivars and selections in the first trial, planted in 2014. Randomized complete block design with four blocks and a single tree of each selection in each block.

| Selection | 10-NutWt | 10-KerWt | Percent kernel |
|---|---|---|---|
| '541.147' | 26.46 | 11.72 | 44.32 |
| 'Thompson' | 27.88 | 12.48 | 44.77 |
| 'Jefferson' | 38.64 | 17.37 | 44.99 |

TABLE 2-continued

Nut weight, kernel weight, percent kernel, and ratings for fiber and blanching (pellicle removal) of 'Thompson' in comparison with other hazelnut cultivars and selections in the first trial, planted in 2014. Randomized complete block design with four blocks and a single tree of each selection in each block.

| | | | |
|---|---|---|---|
| 'McDonald' | 26.96 | 14.05 | 52.15 |
| 'Wepster' | 24.27 | 11.34 | 46.73 |
| LSD (0.05) | 0.70 | 0.34 | 0.52 |

| Selection | Fiber | Blanch |
|---|---|---|
| '541.147' | 3.78 | 4.50 |
| 'Thompson' | 2.19 | 2.75 |
| 'Jefferson' | 2.84 | 4.06 |
| 'McDonald' | 2.59 | 3.50 |
| 'Wepster' | 2.75 | 3.03 |
| LSD (0.05) | 0.20 | 0.24 |

TABLE 3

Frequency of good nuts and of nut and kernel defects in 'Thompson' and other hazelnut cultivars from the first replicated trial, planted in 2014, with 4 trees per selection. Percentages of good nuts and nut kernel defects are averaged over four years (2017-2020).

| Selection | Good | Blank | Brown Stain | Moldy |
|---|---|---|---|---|
| '541.147' | 86.76 | 8.26 | 0.18 | 0.32 |
| 'Thompson' | 83.18 | 4.18 | 0.56 | 2.82 |
| 'Jefferson' | 77.76 | 3.82 | 1.62 | 2.06 |
| 'McDonald' | 84.38 | 3.26 | 0.44 | 2.00 |
| 'Wepster' | 73.82 | 6.00 | 0.12 | 1.00 |
| LSD (0.05) | 3.37 | 1.63 | 0.85 | 1.09 |

| Selection | Shrivel | Poor Fill | Twin | Black Tip |
|---|---|---|---|---|
| '541.147' | 1.88 | 2.50 | 0.12 | 0.00 |
| 'Thompson' | 1.56 | 7.38 | 0.18 | 0.38 |
| 'Jefferson' | 1.44 | 12.62 | 0.62 | 1.00 |
| 'McDonald' | 4.62 | 5.00 | 0.06 | 0.26 |
| 'Wepster' | 0.76 | 17.26 | 0.06 | 1.06 |
| LSD (0.05) | 1.31 | 2.35 | 0.52 | 0.66 |

TABLE 4

Performance of hazelnut selections from the second replicated trial planted in 2015. Trunk cross-sectional area (TCA), annual and cumulative field-run nut yield, and yield efficiency of selections over four years (2018 - 2021). 7 trees per cultivar.

| | TCA | Field-run nut yield (kg/tree) | | | |
|---|---|---|---|---|---|
| Selection[z] | ($cm^2$) | 2018 | 2019 | 2020 | 2021 |
| 'Thompson' | 47 | 1.76 | 2.71 | 3.54 | 6.09 |
| 'Felix' | 122 | 1.00 | 2.81 | 3.93 | 6.96 |
| 'Jefferson' | 74 | 3.00 | 4.66 | 4.51 | 8.93 |
| 'McDonald' | 81 | 1.20 | 4.10 | 6.00 | 8.43 |
| 'Theta' | 123 | 0.57 | 2.11 | 0.59 | 3.64 |
| LSD $_{(.05)}$ | 16 | 0.43 | 0.82 | 0.92 | 1.06 |

TABLE 4-continued

Performance of hazelnut selections from the second replicated trial planted in 2015. Trunk cross-sectional area (TCA), annual and cumulative field-run nut yield, and yield efficiency of selections over four years (2018 - 2021). 7 trees per cultivar.

| | Total field-run yield (kg/tree) | | Yield efficiency (total kg/$cm^2$) | |
|---|---|---|---|---|
| Selection[z] | Nut | Kernel | Nut | Kernel |
| 'Thompson' | 14.10 | 6.20 | 0.30 | 0.13 |
| 'Felix' | 14.70 | 7.47 | 0.12 | 0.06 |
| 'Jefferson' | 21.11 | 9.38 | 0.29 | 0.13 |
| 'McDonald' | 19.73 | 10.26 | 0.24 | 0.13 |
| 'Theta' | 6.91 | 3.52 | 0.06 | 0.03 |
| LSD $_{(.05)}$ | 2.33 | 1.07 | 0.03 | 0.02 |

TABLE 5

Nut weight, kernel weight, kernel percentage, and rating for blanching (pellicle removal) of 'Thompson' and 4 other hazelnut cultivars in the second replicated trial planted in 2015.7 trees per cultivar.

| Selection[z] | Nut weight (g) | Kernel weight (g) | Percent kernel | Blanch |
|---|---|---|---|---|
| 'Thompson' | 2.5 | 1.1 | 44 | 2.4 |
| 'Felix' | 2.5 | 1.2 | 51 | 2.2 |
| 'Jefferson' | 3.4 | 1.5 | 44 | 4.6 |
| 'McDonald' | 2.4 | 1.2 | 52 | 3.2 |
| 'Theta' | 2.1 | 1.0 | 50 | 2.6 |
| LSD $_{(.05)}$ | 0.15 | 0.1 | 1.5 | 0.3 |

TABLE 6

Frequency of good nuts, and of nut and kernel defects of 'Thompson' in comparison with other hazelnut cultivars and selections in the second trial, planted in 2015.

| | Frequency (%) | | | | |
|---|---|---|---|---|---|
| Selection[z] | Good | Blanks | Brown Stain | Mold | Usable Shrivel |
| 'Thompson' | 96.0 | 2.0 | 0.1 | 0.8 | 0.7 |
| 'Felix' | 95.0 | 4.0 | 0.0 | 0.1 | 0.7 |
| 'Jefferson' | 96.0 | 3.1 | 0.0 | 0.5 | 0.8 |
| 'McDonald' | 97.0 | 2.1 | 0.1 | 0.5 | 2.3 |
| 'Theta' | 95.0 | 4.6 | 0.0 | 0.1 | 0.2 |
| LSD $_{(.05)}$ | 2.0 | 2.8 | 0.2 | 0.9 | 1.3 |

| | Frequency (%) | | | | |
|---|---|---|---|---|---|
| Selection[z] | Shrivel | Usable Poor Fill | Poor Fill | Twin | Black Tip |
| 'Thompson' | 0.7 | 1.6 | 0.2 | 0.04 | 0.2 |
| 'Felix' | 0.8 | 0.7 | 0.3 | 0.2 | 0.1 |
| 'Jefferson' | 0.2 | 0.6 | 0.1 | 0.5 | 0.1 |
| 'McDonald' | 0.5 | 1.0 | 0.1 | 0.0 | 0.1 |
| 'Theta' | 0.1 | 0.7 | 0.1 | 0.1 | 0.04 |
| LSD $_{(.05)}$ | 0.8 | 3.9 | 1.2 | 0.7 | 0.4 |

TABLE 7

Primers and annealing temperatures for the microsatellite marker loci used for fingerprinting hazelnut cultivars. Allele size = range of sizes; Primers, forward (F, listed first; 5'-3') and reverse (R, second, 5'-3') (HEX and FAM are dyes); Tm = Annealing temperature; n = Number of alleles; He = expected heterozygosity; Ho = observed heterozygosity; PIC = Polymorphism information content; r = frequency of null alleles; LG = linkage group (S is susceptible female parent 'OSU 252.146'; R is resistant parent 'OSU 414.062'); Reference is the journal article where additional details were published (Gurcan et al., *Tree Genetics and Genomes* 6:513-531, 2010; Gürcan and Mehlenbacher, *Molecular Breeding* 26:551-559, 2010; Bassil, et al., *Acta Horticulturae* 686:105-110, 2005; and Gökirmak, et al. Genetic Resources and Crop Evolution 56:147-172, 2009).

| Locus | Allele sizes | Primer (SEQ ID NO) | Primer (SEQ ID NO) | Tm (° C.) | n | He | Ho | PIC | r | LG | Reference |
|---|---|---|---|---|---|---|---|---|---|---|---|
| A613 | 149-177 | Ned-CACACGC CTTGTC ACTCTTT (1) | R-CCCCTTT CACATG TTTGCTT (2) | 60 | 14 | 0.86 | 0.85 | 0.85 | 0.00 | 11R | Gurcan et al., 2010 |
| A614 | 125-156 | Hex-TGGCAGA GCTTTG TCAGCTT (3) | R-GCAGTGG AGGAT TGCTGACT (4) | 60 | 14 | 0.85 | 0.85 | 0.84 | 0.00 | 6S, 6R | Gurcan et al., 2010 |
| A616 | 136-162 | Fam-CACTCAT ACCGCA AACTCCA (5) | R-ATGGCTT TTGCTT CGTTTTG (6) | 60 | 13 | 0.85 | 0.85 | 0.83 | 0.00 | 8R | Gurcan et al., 2010 |
| A640 | 354-378 | F-TGCCTCT GCAGTT AGTCAT CAAATGT AGG (7) | Fam-CGCCATA TAATTG GGATGC TTGTTG (8) | 67 | 11 | 0.80 | 0.73 | 0.77 | 0.04 | 10R | Gurcan et al., 2010 |
| B617 | 280-298 | Fam-TCCGTGT TGAGTA TGGACGA (9) | R-TGTTTT TGGTGGA GCGATG (10) | 60 | 9 | 0.80 | 0.78 | 0.78 | 0.01 | 8S, 8R | Gurcan et al., 2010 |
| B619 | 146-180 | Fam-AGTCGGC TCCCCT TTTCTC (11) | R-GCGATCT GACCTC ATTTTTG (12) | 60 | 14 | 0.88 | 0.88 | 0.87 | 0.00 | 3S, 3R | Gurcan et al., 2010 |
| B634 | 218-238 | Hex-CCTGCA TCCAGG ACTCATTA (13) | R-GTGCAG AGGTTG CACTCAAA (14) | 60 | 9 | 0.76 | 0.76 | 0.73 | 0.00 | 4R | Gurcan et al., 2010 |
| B657 | 210-228 | Ned-GAGAGTG CGTCTT CCTCTGG (15) | R-AGCCTCA CCTCCA ACGAAC (16) | 60 | 8 | 0.84 | 0.98 | 0.82 | -0.08 | 11S, 11R | Gurcan et al., 2010 |
| B671 | 221-249 | Hex-TTGCCA GTGCATA CTCTGATG (17) | R-ACCAGC TCTGGG CTTAACAC (18) | 60 | 13 | 0.86 | 0.88 | 0.84 | -0.01 | 9S, 9R | Gurcan et al., 2010 |
| B709 | 219-233 | Ned-CCAAGC ACGAAT GAACTCAA (19) | R-GCGGGT TCTCGTT GTACACT (20) | 60 | 8 | 0.74 | 0.76 | 0.70 | -0.01 | 5S, 5R | Gurcan et al., 2010 |

TABLE 7-continued

Primers and annealing temperatures for the microsatellite marker loci used for fingerprinting hazelnut cultivars. Allele size = range of sizes; Primers, forward (F, listed first; 5'-3') and reverse (R, second, 5'-3') (HEX and FAM are dyes); Tm = Annealing temperature; n = Number of alleles; He = expected heterozygosity; Ho = observed heterozygosity; PIC = Polymorphism information content; r = frequency of null alleles; LG = linkage group (S is susceptible female parent 'OSU 252.146'; R is resistant parent 'OSU 414.062'); Reference is the journal article where additional details were published (Gurcan et al., *Tree Genetics and Genomes* 6:513-531, 2010; Gürcan and Mehlenbacher, *Molecular Breeding* 26:551-559, 2010; Bassil, et al., *Acta Horticulturae* 686:105-110, 2005; and Gökirmak, et al. Genetic Resources and Crop Evolution 56:147-172, 2009).

| Locus | Allele sizes | Primer (SEQ ID NO) | Primer (SEQ ID NO) | Tm (° C.) | n | He | Ho | PIC | r | LG | Reference |
|---|---|---|---|---|---|---|---|---|---|---|---|
| B733 | 161-183 | Ned-CACCCT CTTCACC ACCTCAT (21) | R-CATCCC CTGTTGG AGTTTTC (22) | 60 | 8 | 0.68 | 0.68 | 0.63 | 0.00 | 7S, 2R | Gurcan et al., 2010 |
| B749 | 200-210 | Hex-GGCTGA CAACAC AGCAGAAA (23) | R-TCGGCTA GGGTTA GGGTTTT (24) | 60 | 6 | 0.60 | 0.64 | 0.51 | -0.03 | 1R | Gurcan et al., 2010 |
| B751 | 141-153 | Fam-AGCTGGT TCTTCG ACATTCC (25) | R-AAACTC AAATAA AACCCC TGCTC (26) | 60 | 7 | 0.80 | 0.78 | 0.77 | 0.01 | 7S, 2R | Gurcan et al., 2010 |
| B774 | 195-213 | Ned-GTTTTG CGAGCTC ATTGTCA (27) | R-TGTGTGT GGTCTG TAGGCACT (28) | 60 | 8 | 0.80 | 0.80 | 0.77 | 0.00 | 5S, 5R | Gurcan et al., 2010 |
| C115 | 167-225 | Fam-CATTTT CCGCAGA TAATACAGG (29) | R-GTTTCC AGATCTG CCTCCA TATAAT (30) | 60 | 10 | 0.84 | 0.90 | 0.82 | -0.035 | 4S, 4R | Bassil et al., 2005b; Gokirmak et al., 2009 |
| KG807 | 226-248 | F-AAGCAA GAAAGG GATGGT (31) | Fam-CTTACA GATAAAT GGCTCAAA (32) | 54 | 4 | 0.67 | 0.78 | 0.60 | -0.07 | 11 | Gurcan and Mehlenbacher, 2010 |
| KG809 | 333-345 | F-GGAAGG TGAGAG AAATCAAGT (33) | Hex-AGGCAT CAGTTC ATCCAA (34) | 55 | 5 | 0.66 | 0.64 | 0.60 | 0.01 | 4 | Gurcan and Mehlenbacher, 2010 |
| KG811 | 240-278 | F-GAACAA CTGAAG ACAGCAAAG (35) | Ned-AAGGCG GCACTC GCTCAC (36) | 58 | 12 | 0.83 | 0.82 | 0.81 | 0.01 | 2 | Gurcan and Mehlenbacher, 2010 |
| KG827 | 264-282 | Fam-AGAACT CCGACT AATAATC CTAACC CTTGC (37) | R-GAGGGA GCAAGT CAAAGT TGAGAA GAAA (38) | 67 | 9 | 0.78 | 0.84 | 0.75 | -0.04 | 9 | Gurcan and Mehlenbacher, 2010 |

TABLE 7-continued

Primers and annealing temperatures for the microsatellite marker loci used for fingerprinting hazelnut cultivars. Allele size = range of sizes; Primers, forward (F, listed first; 5'-3') and reverse (R, second, 5'-3') (HEX and FAM are dyes); Tm = Annealing temperature; n = Number of alleles; He = expected heterozygosity; Ho = observed heterozygosity; PIC = Polymorphism information content; r = frequency of null alleles; LG = linkage group (S is susceptible female parent 'OSU 252.146'; R is resistant parent 'OSU 414.062'); Reference is the journal article where additional details were published (Gurcan et al., *Tree Genetics and Genomes* 6:513-531, 2010; Gürcan and Mehlenbacher, *Molecular Breeding* 26:551-559, 2010; Bassil, et al., *Acta Horticulturae* 686:105-110, 2005; and Gökirmak, et al. Genetic Resources and Crop Evolution 56:147-172, 2009).

| Locus | Allele sizes | Primer (SEQ ID NO) | Primer (SEQ ID NO) | Tm (° C.) | n | He | Ho | PIC | r | LG | Reference |
|---|---|---|---|---|---|---|---|---|---|---|---|
| KG830 | 279-311 | Ned-TGGAGGA AGTTTT GAATGG TAGTAG AGGA (39) | R-AAAGCA ACTCAT AGCTGA AGTCCA ATC (40)A | 67 | 9 | 0.79 | 0.78 | 0.76 | 0.00 | 9 | Gurcan and Mehlenbacher, 2010 |

TABLE 8

Allele sizes at 20 microsatellite markers in 'Thompson', its parents 'OSU 914.082' and 'OSU 820.007', and ten other cultivars. The same microsatellite markers were used to fingerprint 'OSU 541.147' (US PP33,561) in 2020 and 'PollyO' in 2018. 'Thompson' is easily distinguished from all others as shown in the table below.

| Marker | 'Thompson' | 'OSU 914.082' | 'OSU 820.007' |
|---|---|---|---|
| A613 | 151/153 | 151/169 | 153/161 |
| A614 | 158/158 | 150/158 | 132/158 |
| A616 | 152/152 | 152/152 | 152/160 |
| A640 | 362/362 | 362/374 | 362/362 |
| B617 | 285/293 | 285/293 | 285/293 |
| B619 | 158/158 | 158/166 | 158/166 |
| B634 | 222/228 | 222/228 | 228/236 |
| B657 | 218/226 | 218/226 | 218/224 |
| B671 | 239/243 | 239/239 | 243/243 |
| B709 | 229/229 | 229/229 | 229/229 |
| B733 | 173/185 | 173/181 | 181/185 |
| B741 | 181/190 | 181/190 | 181/181 |
| B749 | 216/216 | 216/216 | 216/216 |
| B751 | 144/null | 144/144 | 152/null |
| B774 | 209/220 | 209/220 | 209/209 |
| C115 | 174/194 | 174/194 | 174/194 |
| KG807 | 242/252 | 242/252 | 242/252 |
| KG809 | 339/342 | 339/342 | 339/342 |
| KG811 | 257/267 | 267/267 | 251/257 |
| KG827 | 270/270 | 270/272 | NA |

| Marker | 'Barcelona' | 'Gasaway' | 'McDonald' |
|---|---|---|---|
| A613 | 153/161 | 161/163 | 153/169 |
| A614 | 125/132 | 143/158 | 135/158 |
| A616 | 144/152 | 150/150 | 150/160 |
| A640 | 354/374 | 362/368 | 362/368 |
| B617 | 285/289 | 291/295 | 293/295 |
| B619 | 158/172 | 172/176 | 158/172 |
| B634 | 228/228 | 222/234 | 222/228 |
| B657 | 218/222 | 224/228 | 210/218 |
| B671 | 225/229 | 237/249 | 229/237 |
| B709 | 227/235 | 229/229 | 229/229 |
| B733 | 173/175 | 175/175 | 173/175 |
| B741 | 181/190 | 190/192 | 181/192 |
| B749 | 216/216 | 214/216 | 214/216 |
| B751 | 144/154 | 144/144 | 144/144 |
| B774 | 209/213 | 209/215 | 209/220 |
| C115 | 174/194 | 214/218 | 174/198 |
| KG807 | 238/252 | 242/252 | 252/252 |
| KG809 | 339/339 | 339/348 | 339/339 |

TABLE 8-continued

Allele sizes at 20 microsatellite markers in 'Thompson', its parents 'OSU 914.082' and 'OSU 820.007', and ten other cultivars. The same microsatellite markers were used to fingerprint 'OSU 541.147' (US PP33,561) in 2020 and 'PollyO' in 2018. 'Thompson' is easily distinguished from all others as shown in the table below.

| | | | |
|---|---|---|---|
| KG811 | 261/267 | 257/261 | 245/267 |
| KG827 | 282/284 | 272/282 | 272/284 |

| Marker | 'Montebello' | 'PollyO' | 'Santiam' |
|---|---|---|---|
| A613 | 151/153 | 153/167 | 151/153 |
| A614 | 125/132 | 125/158 | 132/158 |
| A616 | 152/160 | 144/152 | 150/152 |
| A640 | 362/374 | 354/354 | 362/362 |
| B617 | 285/293 | 285/295 | 285/295 |
| B619 | 160/166 | 158/166 | 158/166 |
| B634 | 232/236 | 228/236 | 222/236 |
| B657 | 218/226 | 218/218 | 218/226 |
| B671 | 225/243 | 229/249 | 225/237 |
| B709 | 229/235 | 223/227 | 229/229 |
| B733 | 175/185 | 175/181 | 175/181 |
| B741 | 181/190 | 168/188 | 190/192 |
| B749 | 216/216 | 216/216 | 216/216 |
| B751 | 154/154 | 144/154 | 144/144 |
| B774 | 209/213 | 209/209 | 215/220 |
| C115 | 174/198 | 194/214 | 194/198 |
| KG807 | 238/242 | 238/252 | 242/252 |
| KG809 | 339/348 | 342/342 | 339/342 |
| KG811 | 251/267 | 261/267 | 257/267 |
| KG827 | 282/282 | 272/284 | 272/272 |

| Marker | 'T.G.d. Langhe' | 'T. Romana' | 'Wepster' |
|---|---|---|---|
| A613 | 153/153 | 153/177 | 159/167 |
| A614 | 125/135 | 125/161 | 135/158 |
| A616 | 150/152 | 150/152 | 152/160 |
| A640 | 368/368 | 372/372 | 368/374 |
| B617 | 285/295 | 285/291 | 293/295 |
| B619 | 150/166 | 158/178 | 166/172 |
| B634 | 228/228 | 222/232 | 228/228 |
| B657 | 218/226 | 218/224 | 226/226 |
| B671 | 239/243 | 229/239 | 239/249 |
| B709 | 229/229 | 227/227 | 229/235 |
| B733 | 173/175 | 175/179 | 173/175 |
| B741 | 181/188 | 168/199 | 181/190 |
| B749 | 216/216 | 216/216 | 214/216 |
| B751 | 150/154 | 144/154 | 144/144 |
| B774 | 209/217 | 209/215 | 209/213 |

TABLE 8-continued

Allele sizes at 20 microsatellite markers in 'Thompson', its parents 'OSU 914.082' and 'OSU 820.007', and ten other cultivars. The same microsatellite markers were used to fingerprint 'OSU 541.147' (US PP33,561) in 2020 and 'PollyO' in 2018. 'Thompson' is easily distinguished from all others as shown in the table below.

| | | | |
|---|---|---|---|
| C115 | 174/174 | 174/198 | 194/194 |
| KG807 | 238/252 | 238/242 | 252/252 |
| KG809 | 339/342 | 339/342 | 342/342 |
| KG811 | 257/267 | 267/267 | 257/257 |
| KG827 | 270/270 | 268/284 | 270/282 |

| Marker | 'Yamhill' |
|---|---|
| A613 | 153/163 |
| A614 | 132/158 |
| A616 | 150/150 |
| A640 | 354/368 |
| B617 | 289/295 |
| B619 | 158/172 |
| B634 | 236/236 |

TABLE 8-continued

Allele sizes at 20 microsatellite markers in 'Thompson', its parents 'OSU 914.082' and 'OSU 820.007', and ten other cultivars. The same microsatellite markers were used to fingerprint 'OSU 541.147' (US PP33,561) in 2020 and 'PollyO' in 2018. 'Thompson' is easily distinguished from all others as shown in the table below.

| | |
|---|---|
| B657 | 218/228 |
| B671 | 225/243 |
| B709 | 229/229 |
| B733 | 181/185 |
| B741 | 181/190 |
| B749 | 216/216 |
| B751 | 152/152 |
| B774 | 209/217 |
| C115 | 198/214 |
| KG807 | 230/252 |
| KG809 | 348/348 |
| KG811 | 251/261 |
| KG827 | 282/282 |

SEQUENCE LISTING

```
Sequence total quantity: 40
SEQ ID NO: 1            moltype = DNA  length = 20
FEATURE                 Location/Qualifiers
source                  1..20
                        mol_type = other DNA
                        organism = synthetic construct
SEQUENCE: 1
cacacgcctt gtcactcttt                                                20

SEQ ID NO: 2            moltype = DNA  length = 20
FEATURE                 Location/Qualifiers
source                  1..20
                        mol_type = other DNA
                        organism = synthetic construct
SEQUENCE: 2
ccccttttcac atgtttgctt                                               20

SEQ ID NO: 3            moltype = DNA  length = 20
FEATURE                 Location/Qualifiers
source                  1..20
                        mol_type = other DNA
                        organism = synthetic construct
SEQUENCE: 3
tggcagagct ttgtcagctt                                                20

SEQ ID NO: 4            moltype = DNA  length = 20
FEATURE                 Location/Qualifiers
source                  1..20
                        mol_type = other DNA
                        organism = synthetic construct
SEQUENCE: 4
gcagtggagg attgctgact                                                20

SEQ ID NO: 5            moltype = DNA  length = 20
FEATURE                 Location/Qualifiers
source                  1..20
                        mol_type = other DNA
                        organism = synthetic construct
SEQUENCE: 5
cactcatacc gcaaactcca                                                20

SEQ ID NO: 6            moltype = DNA  length = 20
FEATURE                 Location/Qualifiers
source                  1..20
                        mol_type = other DNA
                        organism = synthetic construct
SEQUENCE: 6
atggcttttg cttcgttttg                                                20

SEQ ID NO: 7            moltype = DNA  length = 29
```

-continued

```
FEATURE                 Location/Qualifiers
source                  1..29
                        mol_type = other DNA
                        organism = synthetic construct
SEQUENCE: 7
tgcctctgca gttagtcatc aaatgtagg                                        29

SEQ ID NO: 8            moltype = DNA  length = 25
FEATURE                 Location/Qualifiers
source                  1..25
                        mol_type = other DNA
                        organism = synthetic construct
SEQUENCE: 8
cgccatataa ttgggatgct tgttg                                            25

SEQ ID NO: 9            moltype = DNA  length = 20
FEATURE                 Location/Qualifiers
source                  1..20
                        mol_type = other DNA
                        organism = synthetic construct
SEQUENCE: 9
tccgtgttga gtatggacga                                                  20

SEQ ID NO: 10           moltype = DNA  length = 19
FEATURE                 Location/Qualifiers
source                  1..19
                        mol_type = other DNA
                        organism = synthetic construct
SEQUENCE: 10
tgtttttggt ggagcgatg                                                   19

SEQ ID NO: 11           moltype = DNA  length = 19
FEATURE                 Location/Qualifiers
source                  1..19
                        mol_type = other DNA
                        organism = synthetic construct
SEQUENCE: 11
agtcggctcc ccttttctc                                                   19

SEQ ID NO: 12           moltype = DNA  length = 20
FEATURE                 Location/Qualifiers
source                  1..20
                        mol_type = other DNA
                        organism = synthetic construct
SEQUENCE: 12
gcgatctgac ctcatttttg                                                  20

SEQ ID NO: 13           moltype = DNA  length = 20
FEATURE                 Location/Qualifiers
source                  1..20
                        mol_type = other DNA
                        organism = synthetic construct
SEQUENCE: 13
cctgcatcca ggactcatta                                                  20

SEQ ID NO: 14           moltype = DNA  length = 20
FEATURE                 Location/Qualifiers
source                  1..20
                        mol_type = other DNA
                        organism = synthetic construct
SEQUENCE: 14
gtgcagaggt tgcactcaaa                                                  20

SEQ ID NO: 15           moltype = DNA  length = 20
FEATURE                 Location/Qualifiers
source                  1..20
                        mol_type = other DNA
                        organism = synthetic construct
SEQUENCE: 15
gagagtgcgt cttcctctgg                                                  20

SEQ ID NO: 16           moltype = DNA  length = 19
FEATURE                 Location/Qualifiers
source                  1..19
                        mol_type = other DNA
                        organism = synthetic construct
SEQUENCE: 16
agcctcacct ccaacgaac                                                   19
```

-continued

```
SEQ ID NO: 17          moltype = DNA  length = 21
FEATURE                Location/Qualifiers
source                 1..21
                       mol_type = other DNA
                       organism = synthetic construct
SEQUENCE: 17
ttgccagtgc atactctgat g                                          21

SEQ ID NO: 18          moltype = DNA  length = 20
FEATURE                Location/Qualifiers
source                 1..20
                       mol_type = other DNA
                       organism = synthetic construct
SEQUENCE: 18
accagctctg ggcttaacac                                            20

SEQ ID NO: 19          moltype = DNA  length = 20
FEATURE                Location/Qualifiers
source                 1..20
                       mol_type = other DNA
                       organism = synthetic construct
SEQUENCE: 19
ccaagcacga atgaactcaa                                            20

SEQ ID NO: 20          moltype = DNA  length = 20
FEATURE                Location/Qualifiers
source                 1..20
                       mol_type = other DNA
                       organism = synthetic construct
SEQUENCE: 20
gcgggttctc gttgtacact                                            20

SEQ ID NO: 21          moltype = DNA  length = 20
FEATURE                Location/Qualifiers
source                 1..20
                       mol_type = other DNA
                       organism = synthetic construct
SEQUENCE: 21
caccctcttc accacctcat                                            20

SEQ ID NO: 22          moltype = DNA  length = 20
FEATURE                Location/Qualifiers
source                 1..20
                       mol_type = other DNA
                       organism = synthetic construct
SEQUENCE: 22
catcccctgt tggagttttc                                            20

SEQ ID NO: 23          moltype = DNA  length = 20
FEATURE                Location/Qualifiers
source                 1..20
                       mol_type = other DNA
                       organism = synthetic construct
SEQUENCE: 23
ggctgacaac acagcagaaa                                            20

SEQ ID NO: 24          moltype = DNA  length = 20
FEATURE                Location/Qualifiers
source                 1..20
                       mol_type = other DNA
                       organism = synthetic construct
SEQUENCE: 24
tcggctaggg ttagggtttt                                            20

SEQ ID NO: 25          moltype = DNA  length = 20
FEATURE                Location/Qualifiers
source                 1..20
                       mol_type = other DNA
                       organism = synthetic construct
SEQUENCE: 25
agctggttct tcgacattcc                                            20

SEQ ID NO: 26          moltype = DNA  length = 23
FEATURE                Location/Qualifiers
source                 1..23
                       mol_type = other DNA
                       organism = synthetic construct
```

-continued

```
SEQUENCE: 26
aaactcaaat aaaacccctg ctc                                          23

SEQ ID NO: 27          moltype = DNA  length = 20
FEATURE                Location/Qualifiers
source                 1..20
                       mol_type = other DNA
                       organism = synthetic construct
SEQUENCE: 27
gttttgcgag ctcattgtca                                              20

SEQ ID NO: 28          moltype = DNA  length = 21
FEATURE                Location/Qualifiers
source                 1..21
                       mol_type = other DNA
                       organism = synthetic construct
SEQUENCE: 28
tgtgtgtggt ctgtaggcac t                                            21

SEQ ID NO: 29          moltype = DNA  length = 22
FEATURE                Location/Qualifiers
source                 1..22
                       mol_type = other DNA
                       organism = synthetic construct
SEQUENCE: 29
cattttccgc agataataca gg                                           22

SEQ ID NO: 30          moltype = DNA  length = 25
FEATURE                Location/Qualifiers
source                 1..25
                       mol_type = other DNA
                       organism = synthetic construct
SEQUENCE: 30
gtttccagat ctgcctccat ataat                                        25

SEQ ID NO: 31          moltype = DNA  length = 18
FEATURE                Location/Qualifiers
source                 1..18
                       mol_type = other DNA
                       organism = synthetic construct
SEQUENCE: 31
aagcaagaaa gggatggt                                                18

SEQ ID NO: 32          moltype = DNA  length = 21
FEATURE                Location/Qualifiers
source                 1..21
                       mol_type = other DNA
                       organism = synthetic construct
SEQUENCE: 32
cttacagata aatggctcaa a                                            21

SEQ ID NO: 33          moltype = DNA  length = 21
FEATURE                Location/Qualifiers
source                 1..21
                       mol_type = other DNA
                       organism = synthetic construct
SEQUENCE: 33
ggaaggtgag agaaatcaag t                                            21

SEQ ID NO: 34          moltype = DNA  length = 18
FEATURE                Location/Qualifiers
source                 1..18
                       mol_type = other DNA
                       organism = synthetic construct
SEQUENCE: 34
aggcatcagt tcatccaa                                                18

SEQ ID NO: 35          moltype = DNA  length = 21
FEATURE                Location/Qualifiers
source                 1..21
                       mol_type = other DNA
                       organism = synthetic construct
SEQUENCE: 35
gaacaactga agacagcaaa g                                            21

SEQ ID NO: 36          moltype = DNA  length = 18
FEATURE                Location/Qualifiers
source                 1..18
```

-continued

```
                        mol_type = other DNA
                        organism = synthetic construct
SEQUENCE: 36
aaggcggcac tcgctcac                                                  18

SEQ ID NO: 37           moltype = DNA  length = 30
FEATURE                 Location/Qualifiers
source                  1..30
                        mol_type = other DNA
                        organism = synthetic construct
SEQUENCE: 37
agaactccga ctaataatcc taacccttgc                                     30

SEQ ID NO: 38           moltype = DNA  length = 28
FEATURE                 Location/Qualifiers
source                  1..28
                        mol_type = other DNA
                        organism = synthetic construct
SEQUENCE: 38
gagggagcaa gtcaaagttg agaagaaa                                       28

SEQ ID NO: 39           moltype = DNA  length = 29
FEATURE                 Location/Qualifiers
source                  1..29
                        mol_type = other DNA
                        organism = synthetic construct
SEQUENCE: 39
tggaggaagt tttgaatggt agtagagga                                      29

SEQ ID NO: 40           moltype = DNA  length = 27
FEATURE                 Location/Qualifiers
source                  1..27
                        mol_type = other DNA
                        organism = synthetic construct
SEQUENCE: 40
aaagcaactc atagctgaag tccaatc                                        27
```

I claim:

1. A new and distinct variety of *Corylus avellana* plant, substantially as illustrated and described herein.

* * * * *

FIG. 5

Phenology chart 1. Female flowering stage and pollen shed from Dec 2018 - Mar 2019 of OSU 1304.039 and cultivars planted in 2015.

| | Dec | | | Jan | | | | | | Feb | | | | | March | | | |
|---|---|---|---|---|---|---|---|---|---|---|---|---|---|---|---|---|---|---|
| Genotype | 15-Dec | 22-Dec | 30-Dec | 4-Jan | 8-Jan | 15-Jan | 20-Jan | 25-Jan | 30-Jan | 5-Feb | 10-Feb | 15-Feb | 19-Feb | 25-Feb | 3-Mar | 7-Mar | 11-Mar | 18-Mar |
| 1304.039 | | | | | 1 | 10 | 70-10 | 100-20 | 100-70 | -90 | | | | | | | gr tip | RD 1/20 |
| (2 15) | | | | Rd+ | Rd+2 | | Rd+3 | | Rd+3/I | I+3 | | I+3/S+2 | S+3 | | S+3 | | | |
| | | | | | | dark | | | dark | | | dark | dk/blk | | blk | | | |
| Felix | | | | | | | | | 1 | 20 | 40 | 50 | 70 | 80 | 95-10 | | -50 | RD 1/27 |
| (15 21) | | Rd+ | | Rd+ | | Rd+3 | | | Rd+3/I | | I+3 | I+3 | I+2/S+2 | | | | S+3 | |
| | | | | | | dark | | | dark | | | | dark | | | | dk/blk | |
| Jefferson | | | | | | | | 1 | 25 | 40 | 50 | 75 | 100-30 | -50 | -75 | | gr tip | RD 1/20 |
| (1 3) | | | | | | | | | | | Rd | Rd+3 | Rd+3/I | | I+3 | | I+3 | S+3 |
| | | | | | | | | | | | red | | | | red/dk | | dark | dk/blk |
| McDonald | | | | | | 1 | 75 | 100-20 | -90 | -95 | | | | | gr tip | | | RD 1/20 |
| (2 15) | Rd | | | | Rd+2 | | Rd+3 | Rd/I | Rd/I+ | I+3 | | | I+/S+3 | S+3 | | | S+3 | |
| | | | | | | | | dark | | | | | | dark | | | black | |
| Theta | | | | | | | | | | | | | | 1 | 30 | 50 | 75 | 100-50 |
| (5 15) | | Rd | | | | Rd+2 | | | Rd+3 | | | Rd+2/I | | | I+2/S+2 | | S+3 | S+3 |
| | | | | | | | | | | | | | | | red/dk | | rd/dk | dk/blk |

Flower stages: RD = Red dot; I = styles protruding ~1-3mm, straight; S = First appearance of 'spiders' or flowers with reflexed styles, and S+3 = Green = Pollen shed (a minus sign in front of the number indicates the percent of catkins that have already shed out).
Red = Female flowers; red, blk (black), dk (dark, not quite red, not yet black).

FIG. 6

Phenology chart 2. Female flowering and pollen shed from Dec 2019 - Mar 2020 of OSU 1304.039 and hazelnut cultivars planted in 2015.

| | Dec | | | Jan | | | | | | Feb | | | | | March | | | |
|---|---|---|---|---|---|---|---|---|---|---|---|---|---|---|---|---|---|---|
| Genotype | 15-Dec | 22-Dec | 30-Dec | 4-Jan | 8-Jan | 15-Jan | 20-Jan | 25-Jan | 30-Jan | 5-Feb | 10-Feb | 15-Feb | 19-Feb | 25-Feb | 3-Mar | 7-Mar | 11-Mar | 18-Mar |
| 1304.039 | | | | | 10 | 40 | 80-20 | -80 | | | | | | gr tip | | | RB 3-11 | |
| (2 15) | | | | | Rd | | Rd+2 | Rd/I | I+2 | I/S+3 | S+3 | | S+3 | | | | | |
| | | | | | | | | | dk | | dk/blk | | blk | | | | | |
| Felix | | | | | | | 1st | 20 | 50 | 85 | 95-30 | | | | | | gr tip | RB 3-21 |
| (15 21) | | | | | | Rd | Rd+2 | | | I+2/S+2 | I+2/S+3 | | | S+3 | | | | |
| | | | | | | | | | | dk | | | | dk/blk | | | | |
| Jefferson | | | | | | | | 1st | 50 | 95-20 | -75 | -85 | -95 | | gr tip | | | RB 3-18 |
| (1 3) | | | | | | | | | | Rd/I | | | Rd/I+2 | I+2/S+2 | S+3 | | S+3 | |
| | | | | | | | | | | red | red | | red | dk | red/dk | | dk | |
| McDonald | | | | 1st | 25 | 95 | -90 | | | gr tip | | | | | RB 3-3 | | | |
| (2 15) | | | | | | Rd/I | I+3 | I+2/S | I+2/S+2 | I/S+3 | I+3/S+3 | | | I+2/S+3 | S+3 | | | |
| | | | | | | Red | | | Red | dk | | | | dk | dk/blk | | | |
| Theta | | | | | | | | | | 1 | 5 | | 25 | 75 | 98-30 | | -95 | RB 3-29 |
| (5 15) | | | | | | | | | | Rd | Rd+2 | | Rd+3/I | I+3/S | | | I+2/S+2 | |
| | | | | | | | | | | | | | Red | Red/dk | | | red/dark | |

Flower stages: RD = Red dot; I = styles protruding ~1-3mm, straight; S = First appearance of 'spiders' or flowers with reflexed styles, and S+3 = majority of flowers are in 'spider' or fully reflexed stage.

Green = Pollen shed (a minus sign in front of the number indicates the percent of catkins that have already shed out).

Red = Female flowers; red, blk (black), dk (dark, not quite red, not yet black).

FIG. 7

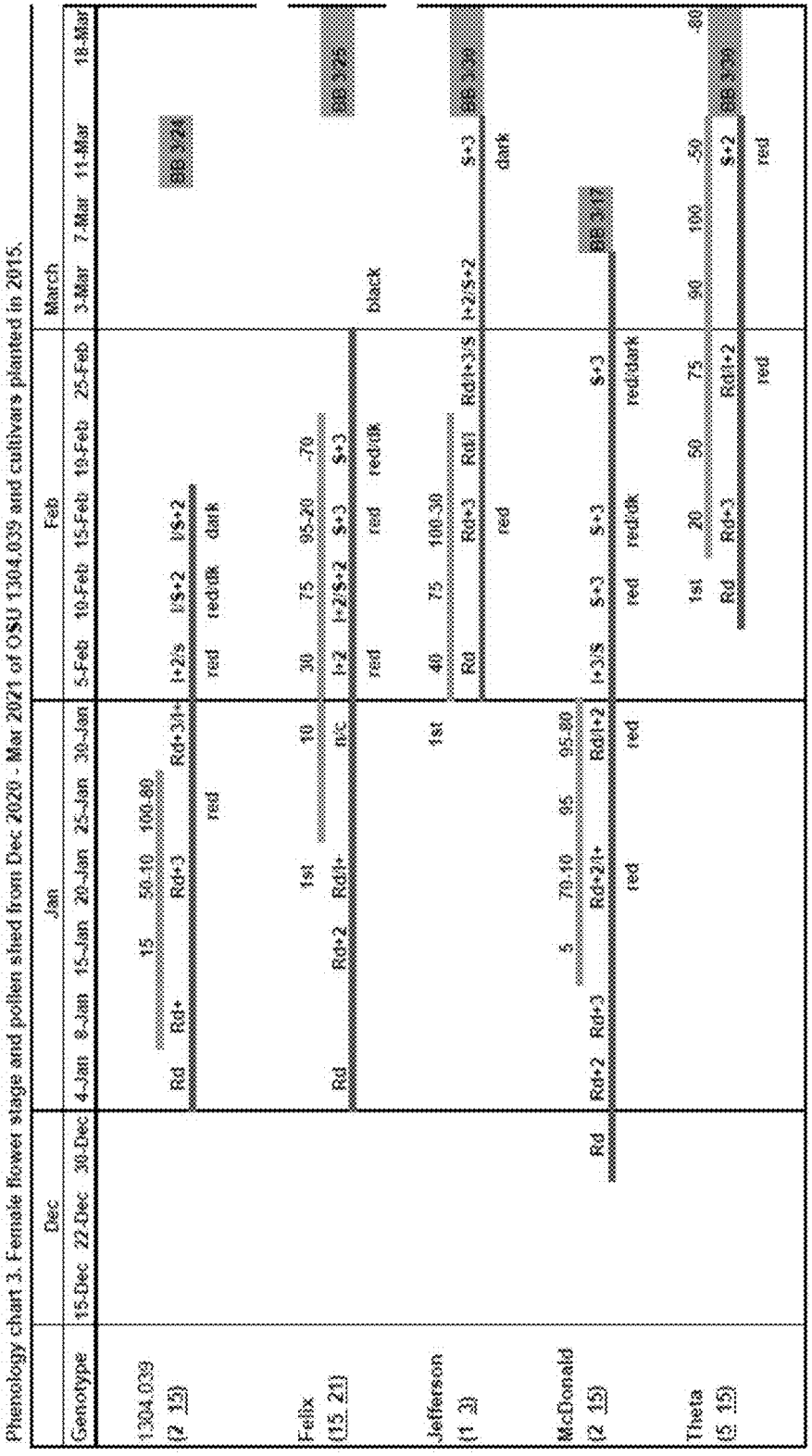

Flower stages: RD = Red dot; I = styles protruding ~1-3mm, straight; S = First appearance of 'spiders' or flowers with reflexed styles, and S+3 = majority of flowers are in 'spider' or fully reflexed stage.

Green = Pollen shed (a minus sign in front of the number indicates the percent of catkins that have already shed out).

Red = Female flowers; red, blk (black), dk (dark, not quite red, not yet black).